(12) United States Patent
Bazan et al.

(10) Patent No.: US 7,968,487 B2
(45) Date of Patent: Jun. 28, 2011

(54) SINGLE COMPONENT, PHOSPHINE-FREE, INITIATORS FOR ETHYLENE HOMOPOLYMERIZATION AND COPOLYMERIZATION WITH FUNCTIONALIZED CO-MONOMERS

(75) Inventors: Guillermo C. Bazan, Santa Barbara, CA (US); Rene' Rojas, Santiago (CL)

(73) Assignee: The Regents of the University of California, Oakland, CA (US)

( * ) Notice: Subject to any disclaimer, the term of this patent is extended or adjusted under 35 U.S.C. 154(b) by 1167 days.

(21) Appl. No.: 11/649,949

(22) Filed: Jan. 5, 2007

(65) Prior Publication Data
US 2007/0225456 A1 Sep. 27, 2007

Related U.S. Application Data

(63) Continuation-in-part of application No. 10/377,491, filed on Feb. 28, 2003, now Pat. No. 7,259,214, and a continuation-in-part of application No. 10/378,957, filed on Mar. 3, 2003, now Pat. No. 7,754,839.

(51) Int. Cl.
*C08F 4/80* (2006.01)

(52) U.S. Cl. ........ 502/155; 502/152; 502/162; 502/167; 526/115; 526/117; 526/161; 526/171; 526/172; 556/136; 556/137; 556/138; 556/140; 556/146

(58) Field of Classification Search .......... 502/155, 502/162, 167; 526/115, 117, 161, 171, 172; 556/136, 137, 138, 140, 146
See application file for complete search history.

(56) References Cited

U.S. PATENT DOCUMENTS

| 6,174,976 B1 | 1/2001 | Killian et al. |
| 2004/0024149 A1 | 2/2004 | Bazan et al. |

FOREIGN PATENT DOCUMENTS

| WO | WO 98/42664 | | 10/1998 |
| WO | WO 98/42665 | * | 10/1998 |
| WO | WO 00/20464 | | 4/2000 |
| WO | WO 01/92348 | | 12/2001 |
| WO | WO 01/92348 A2 | | 12/2001 |

OTHER PUBLICATIONS

Bonnet, M. C.; Dahan, F.; Ecke, A.; Keim, W.; Schultz, R. P.; Tkatchenko, I. Chem Commun. 1994, 615.
Galli, P.; Vecellio, G. J. Polym. Sci. Part A: Polym. Chem. 2004, 42, 396.
S. J. Diamanti, V. Khanna, A. Hotta, D. Yamakawa, F. Shimizu, E. J. Kramer, G. H. Fredrickson, and G. C. Bazan. J. Am. Chem. Soc., 2004, 126, 10528-10529.
Younkin, Todd R., et al. Neutral, Single-Component Nickel (II) Polyolefin Catalysts That Tolerate Heteroatoms, Science, (2000) 287, 460-462.
Boffa, L. S.; Novak, B. M. Chem. Rev. 2000, 100, 1479.
Mecking, S. Coordination Chemistry Reviews 2003, 203, 325.
Yanjarappa, M. J.; Sivaram, S. Prog. Polym. Sci. 2002, 27, 1347.
Mecking, S.; Held, A.; Bauers, F. M. Angew. Chem., Int. Ed. 2002, 41, 544.
Gibson, V. C.; Spitzmesser, S. K. Chem. Rev. 2003, 103, 283. 283.
Flack, H. D. Acta. Cryst. 1983 A39, 876.
Keim, W.; Kowalt, F. H.; Goddard, R.; Kruger, C. Angew. Chem., Int. Ed. Engl. 1978,17, 466.
Ittel, S. D. et al., "Late-Metal Catalysts for Ethyleen Homo- and Copolymerization," Chem. Rev. 100(4):1169-1203 (2000).
Gates, D. P. et al., "Synthesis of Branched Polyethylene Using (∀-Diimine) nickel(II) Catalysts: Influence of Temperature, Ethylene Pressure, and Ligand Structure on Polymer Properties," Macromolecules 33:2320-2334 (2000).
Svejda, S. A. et al., "Low-Temperature Spectroscopic Observation of Chain Growth and Migratory Insertion Barriers in (∀-Diimine)Ni(II) Olefin Polymerization Catalysts," J. am. Chem. Soc. 121:10634-10635 (1999).
Younkin, T. R. et al., "Neutral, Single-Component Nickel (II) Polyolefin Catalysts That Tolerate Heteroatoms," Science 287:460-462 (2000).
Lee, B. Y. et al., "∀-Iminocarboxamidato—Nickel(II) Ethylene Polymerization Catalysts," J. Am. Chem. Soc. 123:5352-5353 (2001).
Coates, G. W. et al., "Catalysts for the Living Insertion Polymerization of Alkenes: Access to New Polyolefin Architectures Using Ziegler-Natta Chemistry," Angew. Chem. Int. Ed. 41:2236-2257 (2002).
Jansen, J.C. et al., "Evidence of the Quasi-Living Character of the ansa-Zirconocene/MAO—Catalyzed Copolymerization of Ethylene and Norbornene," Macromol. Rapid Commun. 22(17):1394-1398 (2001).
Schunn, R.A. et al., "BIS(1,5-Cyclooctadiene)Nickel(0)," Inorg. Synth. 28:94-98 (1990).
Tomov A et al. "Binuclear Nickel-Ylide Complexes as Effective Ethylene Oligomerizaton/Polymerization Catalysts" Journal of Molecular Catalysis, Lausanne, Ch, vol. 103, No. 2, 1995, pp. 95-103, XP000853887, table 4.
Soula, R. et al. "Very Active Neutral P,O-Chelated Nickel Catalysts for Ethylene Polymerization" Macromolecules, 34(8), 2438-2442 Coden: Mamobx; ISSN: 0024-9297, 2001, XP199852 See right hand column concerning compound 6, p. 2440.
Kurtev K et al: "Ethene Polymerization by Binuclear Nickel-Ylide Complexes" Journal of Molecular Catalysis, Lausanne, CH, vol. 88, No. 2, 1994, pp. 141-150, XP000853888, table 1.

(Continued)

*Primary Examiner* — Roberto Rabago
(74) *Attorney, Agent, or Firm* — Berliner & Associates

(57) ABSTRACT

Novel phosphine-free non-ionic single catalysts, and method for making such catalysts, for the homo-polymerization and copolymerization of olefins such as ethylene, α-olefins and functionalized olefins without the use of additional co-activators, are disclosed. These phosphine-free non-ionic single catalysts are also active for co-polymerization of olefins with monomers with polar functionalities. The catalyst of this invention comprise of a late transition metal with a chelating monoanionic ligand, an R group and a neutral 2 electron donor ligand. Catalysts are prepared by the oxidative addition of benzylhalide (halide=Cl, Br or I) to an appropriate metal source in the presence of a stabilizing agent, such as nitrogen based ligands, followed by the addition of the deprotonated form of the chelating ligand.

7 Claims, 4 Drawing Sheets

OTHER PUBLICATIONS

Bun Yeoul Lee et al: "Alpha-Iminocarboxamidato-Nickel (II) Ethylene Polymerization Catalysts" Journal of the American Chemical Society, American Chemical Society, Washington, DC, US, vol. 22, No. 123, 2001, pp. 5352-5353, XP001066396 ISSN: 0002-7863, cited in the application, the whole document.

Diamanti S J, et al: "Ethylene Homopolymerization and Copolymerization with Functionalized 5-Norbornen-2-YI Monomers by a Novel Nickel Catalyst System" Macromolecules, American Chemical Society, East, US, vol. 36, No. 26, Dec. 30, 2003, pp. 9731-9735, XP001190698 ISSN: 0024-9297, the whole document.

International Search Report, dated Sep. 7, 2004, PCT/US04/006301.

Written Opinion of the International Searching Authority, 2004, PCT/US04/006301.

"Ethylene Homopolymerization and Copolymerization with Functionalized 5-Norbornen-2-yl Monomers by a Novel Nickel Catalyst System"; By S.J. Diamanti, P. Ghosh, F. Shimizu and G. Bazan; Macromolecules 2003, 36, 9731-9735.

"α-Iminocarboxamidato—Nickel (II) Ethylene Polymerization Catalyst"; By. B.Y. Lee, G.C. Bazan, J. Vela, Z.J.Komon and X. Bu; J. American Chem. Soc. 2001, vol. 123, pp. 5352-5353.

"Boron Trifluoride Activation of Ethylene Oligomerization and Polymerization Catalysts"; By Z.J.A. Komon; G.C. Bazan, C. Fang and X. Bu; Inorganica Chimica Acta, vol. 345, (2003) pp. 95-102.

"Controlled Polymerization of β-Lactamus Using Metal-Amido Complexes: Synthesis of Block Copoly (β-peptides)"; By J. Cheng and T.J. Deming; J. American Chem. Soc. 2001, vol. 123, pp. 9457-9458.

Holger Frauenrath, et al., "Single Component Zirconocene Catalysts for the Stereospecific Polymerization of MMA", pp. 97-108, 2003.

Philipp Walter, et al., "Correlations Between Chain Branching, Morphology Development and Polymer Properties of Polyethenes", pp. 317-326 2003.

Riccardo PO, et al. "A Comparison of the Behavior of Nickel/MAO Catalytic Systems in the Polymerization of Styrene and 1,3-Cyclohexadiene", pp. 365-374, 2003.

Aleksander Ostoja Starzewski, "Nickel Polymerization Catalysts with Ylide Steering Ligands", pp. 1-26, 2001.

Jurgen Kukral, "Microstructure Control of Ethene Homopolymers Through Tailored Ni,Pd(II) Catalysts", pp. 27-58, 2001.

Gerrit A. Luinstra, et al., "Highly Active Ethene Polymerization Catalysts with Unusual Imine Ligands", pp. 59-99, 2001.

Brian L. Goodall, "Cycloaliphatic Polymers via Late Transition Metal Catalysis", pp. 101-154, 2001.

Michael R. Buchmeiser, "Well-Defined Transition Metal Catalysts for Metathesis Polymerization", pp. 155-191, 2001.

Stephen E. Lehman, Jr., et al. "Catalysis in Acyclic Diene Metathesis (ADMET) Polymerization", pp. 193-229, 2001.

Stefan Mecking, et al., "Transition Metal-Catalyzed Polymerization in Aqueous Systems", p. 231-278, 2001.

Giambattista Consiglio, "Copolymerization of Carbon Monoxide with Alkenes", pp. 279-305, 2001.

Ayusman Sen, et al., "Strategies for Catalytic Polymerization of Polar Monomers", pp. 307-317, 2001.

* cited by examiner

1

2

3

4

SINGLE COMPONENT, PHOSPHINE-FREE, INITIATORS FOR ETHYLENE HOMOPOLYMERIZATION AND COPOLYMERIZATION WITH FUNCTIONALIZED CO-MONOMERS

CROSS-REFERENCE TO RELATED APPLICATIONS

This application is a continuation in part of U.S. patent application Ser. No. 10/377,491, filed on Feb. 28, 2003, now U.S. Pat. No. 7,259,214, and U.S. patent application Ser. No. 10/378,957, filed on Mar. 3, 2003, now U.S. Pat. No. 7,754,839, both of which are incorporated by reference herein.

FIELD OF INVENTION

This invention relates generally to the polymerization and co-polymerization of olefins with functionalized monomers, more particularly, to a method for the polymerization and co-polymerization of olefins with functionalized monomers using phosphine-free non-ionic late transition metal single component catalysts, without the need for co-activators.

BACKGROUND OF THE INVENTION

In the last few years several catalysts have been reported for olefin polymerization. The polymerization catalysts reported by Brookhart perform in the presence of methylaluminoxanes and Lewis acids (1). Several patents have been filed based on these catalysts, (See WO09623010 and references therein). These catalyst systems are thermally unstable and the activity of the methylaluminoxane activated catalysts decays rapidly at 60° C. (2), and the borane activated catalysts are decomposed at room temperature (3). Another type of catalyst is those reported by Younkin et al., (4). These are neutral species that do not require an activator. However, they are prone to an induction period and lower activity compared with the cationic Brookhart systems. PCT application WO01/92348 describes the polymerization of ethylene and the co-polymerization of ethylene using zwitterionic nickel complexes that require the presence of a Lewis acid. Lewis Acids are deactivated by functionalities and they promote unwanted secondary reactions, e.g., chain transfers that are detrimental to the polymer chain growth.

Despite the foregoing, interest in metal-mediated polymerization of olefins remains unabated in academic and industrial laboratories (5, 6, 7, 8, 9, 10, 11, 12, 13, 14). Furthermore, despite the foregoing, there is a need in the field for single component catalytic systems that offer better control over polymerization reactions and lower overall costs.

BRIEF SUMMARY OF THE INVENTION

The present invention fulfills the need for a method of both ethylene homo-polymerization and co-polymerization of ethylene with functional co-monomers, using a phosphine-free non ionic catalyst without the requirement of additional co-activators.

The catalyst of the present invention has a general formula of:

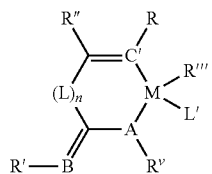

wherein:

M represents a late transition metal ion, preferably selected from Fe, Co, Ni, Pd and Cu.

A, B and C' represent oxygen, nitrogen, phosphorus, carbon, or sulfur atoms.

L represents a saturated or unsaturated bridging hydrocarbon unit i.e., —$(CH_2)_n$—, n=0-3; —CH═CH—, and aromatic units.

R represents a $C_1$-$C_{24}$ hydrocarbon selected from alkyl, alkene, hydrocarbyl, cycloalkyl, aryl or substituted aryl; also the aryl substituents could be functionalized groups that increase or decrease the electron density or modify the steric encumbrance at C'.

R' represents those hydrocarbons described by R, but R and R' are not necessarily equivalent.

R" represents a hydrocarbon $C_1$-$C_{24}$ hydrocarbon selected from alkyl, alkene, hydrocarbyl, cycloalkyl, aryl, substituted aryl, O-hydrocarbon, O-aryl, O-substituted aryl; also the substituent could be a halogen.

L' represents a neutral monodentate 2e⁻ N-base donor ligand

L' can also represent a neutral monodentate 2e⁻ O-base ligand i.e., O═P($R^{iv}$)$_3$; $R^{iv}$COR$^{iv}$, Furan, $R^{iv}$OR$^{iv}$, 1,4-dioxane, ($R^{iv}$)$_3$NO.

$R^{iv}$ represents a hydrogen, hydrocarbon, alkyl, alkene, hydrocarbyl, cycloalkyl, aryl or substituted aryl.

R''' represents a hydrocarbon, alkyl, alkene, hydrocarbyl, allyl, aryl, substituted aryl, benzyl, substituted benzyl, (C═O)-alkyl, (C═O)-aryl or substituted (C═O)-aryl.

R''' and L' may be combined into a single, chelating fragment,

Rv=R only when A=phosphorous, carbon, or nitrogen.

In one embodiment, a phosphine-free non ionic catalyst is formed via the oxidative addition of alkyl or acid halide to an appropriate metal source (i.e., Ni(COD)$_2$, Ni(CH$_2$═C(CH$_3$)CH$_2$)$_2$, Pd(dba)$_2$, Pd(P(C$_4$H$_9$)$_3$)$_2$, etc.) in the presence of a stabilizing agent, such as a nitrogen containing ligand, followed by the addition of the deprotonated chelating ligand.

The present invention also discloses using the phosphine-free non ionic catalyst for co-polymerization of olefins with functionalized monomers with functionalities such as alcohols (preferably, 5-norbornen-2-ol) and acetates (preferably, 5-norbomen-2-yl acetate). Additional functionalities include olefins with cyano, keto, alkyl/aryl halides, nitro and sulfanate groups.

In yet another embodiment, the invention provides for polymerizing an olefin with a phosphine-free non ionic catalyst selected from the group consisting of a compound of the formula $R^1$CH═CH$_2$, cyclopentene, styrene, norbornene and/or polar olefins such as $H_2$C═CH(CH$_2$)nCO$_2$R$^2$, substituted cyclopentene, styrene, norbornene derivatives bearing functional groups, where $R^1$ can be hydrogen, alkyl, a substituted alkyl bearing functional groups (OH, NH2, etc), where $R^2$ can be hydrogen or alkyl; or a combination thereof, and n is an integer from 0 to 100.

These new single component catalysts provide a convenient route to polyolefin materials with enhanced properties such as hydrophilicity, thereby significantly increasing the utility of these materials for various commercial purposes.

BRIEF DESCRIPTION OF THE DRAWINGS

For a more complete understanding of the present invention, reference is now made to the following descriptions taken in conjunction with the accompanying drawing in which.

DETAILED DESCRIPTION OF THE INVENTION

Figure 1:
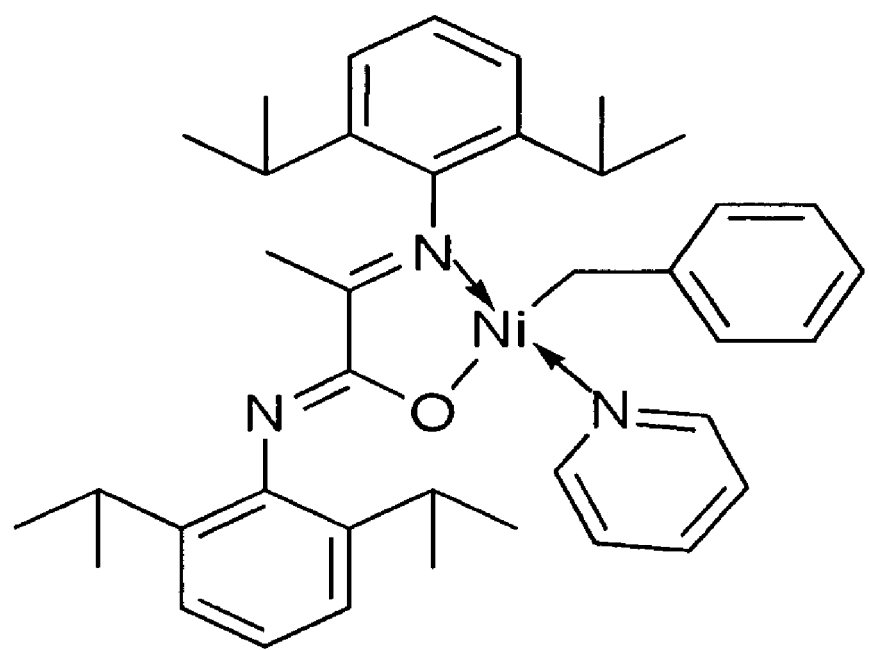
FIG. 1 shows a representation of the molecular structure of initiator 1 drawn at 50% probability. Hydrogen atoms were removed for clarity.

The invention provides a novel phosphine-free non-ionic single catalyst, and method for making such catalysts, for the homo-polymerization and copolymerization of olefins such as ethylene, α-olefins and functionalized olefins without the use of additional co-activators. These catalysts are also active for co-polymerization of olefins with monomers with polar functionalities.

The general catalytic initiators of this invention comprise of a late transition metal with a chelating monoanionic ligand, an R group and a neutral 2 electron donor ligand. The initiators of the present invention are represented by the generic following structure:

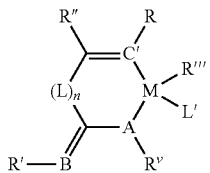

wherein:

M represents a late transition metal ion, preferably selected from Fe, Co, Ni, Pd and Cu.

A, B and C' represent oxygen, nitrogen, phosphorus, carbon, or sulfur atoms.

L represents a saturated or unsaturated bridging hydrocarbon unit i.e., $-(CH_2)_n-$, n=0-3; $-CH=CH-$, and aromatic units.

R represents a $C_1$-$C_{24}$ hydrocarbon selected from alkyl, alkene, hydrocarbyl, cycloalkyl, aryl or substituted aryl; also the aryl substituents could be functionalized groups that increase or decrease the electron density or modify the steric encumbrance at C'.

R' represents those hydrocarbons described by R, but R and R' are not necessarily equivalent.

R" represents a hydrocarbon $C_1$-$C_{24}$ hydrocarbon selected from alkyl, alkene, hydrocarbyl, cycloalkyl, aryl, substituted aryl, O-hydrocarbon, O-aryl, O-substituted aryl; or a halogen.

L' represents a neutral monodentate $2e^-$ N-base donor ligand i.e.,

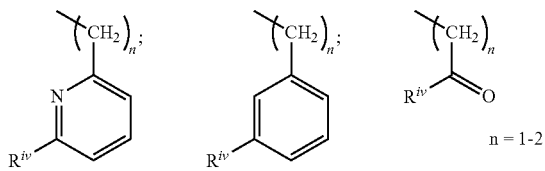

L' can also represent a neutral monodentate $2e^-$ O-base ligand i.e., $O=P(R^{iv})_3$; $R^{iv}COR^{iv}$, Furan, $R^{iv}OR^{iv}$, 1,4-dioxane, $(R^{iv})_3NO$.

$R^{iv}$ represents a hydrogen, hydrocarbon, alkyl, alkene, hydrocarbyl, cycloalkyl, aryl or substituted aryl.

R''' represents a hydrocarbon, alkyl, alkene, hydrocarbyl, allyl, aryl, substituted aryl, benzyl, substituted benzyl, (C=O)-alkyl, (C=O)-aryl or substituted (C=O)-aryl.

R''' and L' may be combined into a single, chelating fragment, examples are represented by:

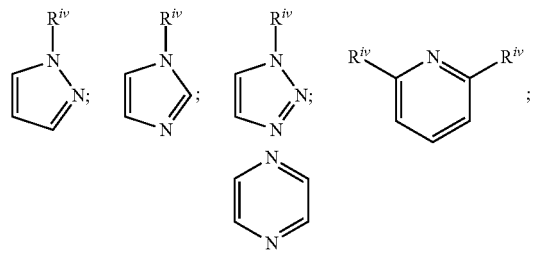

n = 1-2

Rv=R only when A=phosphorous, carbon, or nitrogen.

The initiators are prepared by the oxidative addition of benzylhalide (halide=Cl, Br or I) to an appropriate metal source in the presence of a stabilizing agent, such as nitrogen based ligands, followed by the addition of the deprotonated form of the chelating ligand. The metal source includes, but are not limited to, $Ni(COD)_2$, $Ni(CH_2=C(CH_3)CH_2)_2$, $Pd(dba)_2$, and $Pd(P(C_4H_9)_3)_2$. In one embodiment, the stabilizing agent is a nitrogen containing ligand.

In the presence of a single component catalytic initiator, as disclosed, polymerization and copolymerization of olefins occur at temperatures from −30° C. to 100° C. These olefins include, but are not limited to, $R^1CH=CH_2$, cyclopentene, styrene, norbornene and/or polar olefins such as $H_2C=CH$ $(CH_2)_nCO_2R^2$, substituted cyclopentene, styrene, norbornene derivatives bearing functional groups, where $R^1$ can be hydrogen, alkyl, a substituted alkyl bearing functional groups (OH, $NH_2$, etc), and n is an integer from 0 to 100. In a preferred embodiment, the trimethylphosphine-free non ionic catalyst is used for co-polymerization of olefins with 5-norbornen-2-ol and 5-norbornen-2-yl acetate. Additional functionalities include olefins with cyano, keto, alkyl/aryl halides, nitro and sulfanate groups. Additionally $R^2$ can be hydrogen or alkyl.

Crystallographic characterization of these catalytic initiators was performed by placing a monocrystal of the initiator on a glass fiber and transferring it to a Bruker CCD platform diffractometer. The SMART (15) program package was used to determine the unit-cell parameters and for data collection (25 sec/frame scan time for a sphere of diffraction data). The raw frame data was processed using SAINT (16) and SADABS (17) yielded the reflection data file. Subsequent calculations were carried out using the SHELXTL (18) program. The structure was solved by direct methods and refined on $F^2$ by full-matrix least-squares techniques. The analytical scattering factors (19) for neutral atoms were used throughout the analysis. Hydrogen atoms were located from a difference-Fourier map and refined (x, y, z and $U_{iso}$) (20). Single crystals of initiators 1, 2 and 4 suitable for x-ray diffraction studies were obtained by evaporation of Benzene or diffusion of pentane into a benzene or toluene solution.

NMR spectra of catalytic initiators 1-4 were obtained using Varian Unity 400 and 500 spectrometers. $^1H$ NMR samples were prepared under inert conditions using 10 mg of sample in 1 mL of d-benzene. $^{13}C$ NMR samples were prepared in a similar manner to those for $^1H$ NMR but using 25 mg of sample. All NMR samples were run at room temperature.

Polymer samples were characterized by GPC analysis at 135° C. in o-dichlorobenzene (in a Polymers Laboratories, High Temperature Chromatograph, PI-GPC 200) relative to universal calibration from polystyrene standards. Samples were prepared by weighing 6.5-8 mg of polymer and dissolving them in 5 mL of o-dichlorobenzene at 135° C. Samples were then filtered at 135° C. through a 1 μm laminated teflon filter into a capped vial (21).

NMR spectra of copolymer samples were obtained using a Varian Unity 500 spectrometer. $^1$H NMR spectra of the polymers were obtained with 25-30 mg of polymer dissolved in a mixed solvent ($C_6D_6$ 1,2,4-trichlorobenzene in a 1:4 volume ratio) at 115° C. Integration of the functional group peak compared to the integration of the backbone peak gives the % monomer incorporation into the backbone per 1000 carbon units (21).

The following examples will illustrate best practices of the invention.

Example 1

Catalytic initiator 1: N-(2,6-Diisopropylphenyl)-2-(2,6-diisopropylphenylimino)propanamidato-κ$^2$N,O (η$^1$-CH$_2$Ph)nickel(pyridine)

The synthesis of initiator 1 was carried out under an inert atmosphere with minimal exposure to light. A Ni(COD)$_2$ solution (68 mg, 0.25 mmol in 5 mL of THF) was treated with a mixture of benzyl chloride (63 mg, 0.63 mmol) and pyridine (234 mg, 2.96 mmol) in 2 mL of THF at 35° C. or ambient temperature. The potassium salt of the ligand (108 mg, 0.24 mmol, dissolved in 3 mL of THF) was added after 10 minutes. The reaction mixture was allowed to warm up to room temperature and was stirred overnight, volatiles were then removed under vacuum. The resulting oil was extracted with ether (15 mL) and filtered. Initiator 1 was isolated from the first crystallization batch as dark orange crystals in 62% yield. $^1$H NMR spectroscopy showed 2 isomers in a 3:1 ratio, which are positional isomers having N,O ligand coordination with the benzyl group positioned either in a cis or trans orientation relative to the carboxamide group.

$^1$H-NMR (399.95 MHz, [d$_6$]-benzene, 298 K): Major isomers; δ=7.91 (d, 1H), 7.40 (d, 1H), 7.14-6.95 (m, 6H), 6.80-6.73 (m, 3H), 6.71-6.63 (m, 3H), 6.24 (t, 1H), 5.83 (t, 2H), 3.90 (sep 2H), 3.54 (sep 2H), 2.09 (s, 3H), 1.58 (dd 12H), 1.39 (d, 12H), 1.42 (s, 2H), Minor isomers; 3.64 (sep 2H), 3.31 (sep 2H), 2.07 (s, 3H) 1.40 (d, 12H, CH$_3$-i-Pr), 1.17 (d, 6H, CH$_3$-i-Pr).

Single crystals of the initiator 1 suitable for crystallographic studies were obtained from benzene by slow evaporation at RT and the results are shown in FIG. 1. The molecular connectivity is consistent with N,O-coordinated structures and support the 1H-NMR spectroscopy assignment. There is a distortion of the square-planar geometry around nickel. The benzyl group is coordinated in an η$^1$-fashion, with the methylene group in a trans orientation relative to carboxamide nitrogen atom. The benzyl fragment is tilted 7° out of the plane defined by N(1)-Ni—O. The N(1)-Ni—N(3) angle 169.87(10)° is smaller than 180° and the N(3) atom is 10° out of the N(1)-Ni—O plane. The bond distances for Ni—O(1), Ni—N(1), Ni—C(28) and Ni—N(3) are (1.9267(19) Å, 1.915(2) Å, 1.943(3) Å and 1.888(2) Å, respectively.

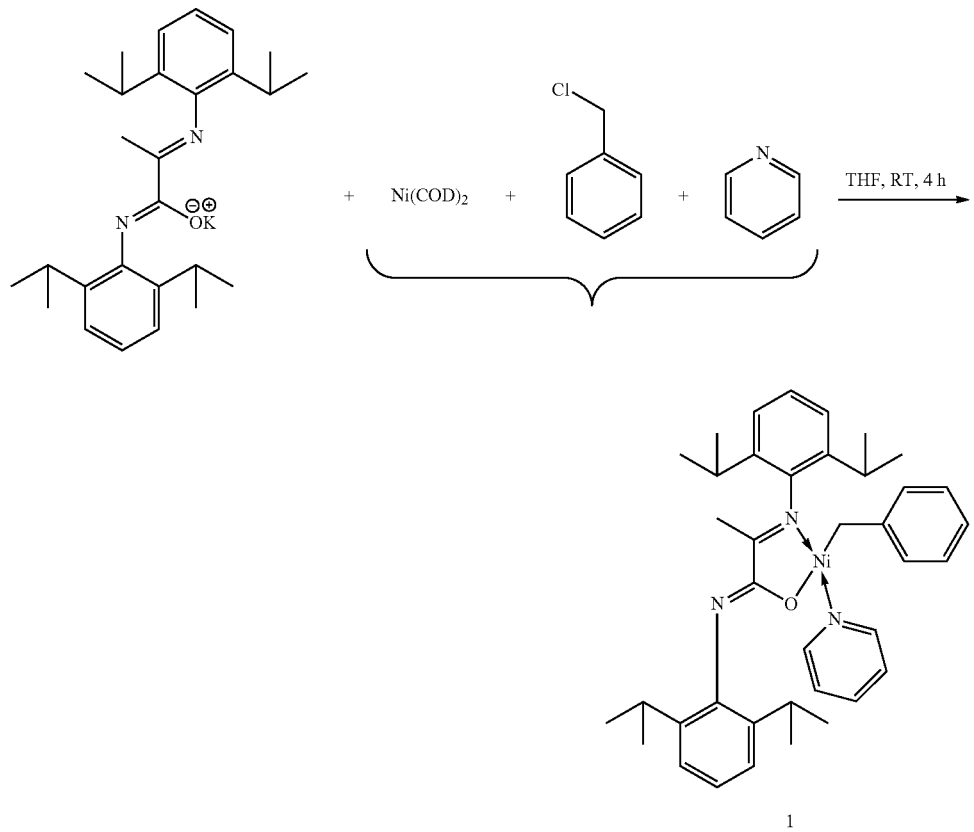

Example 2

Catalytic initiator 2: [N-(2,6-Diisopropylphenyl)-2-(2,6-diisopropylphenylimino)propanamidato-κ²N,O](η¹CH₂Ph)nickel(2,6-dimethylpyridine)

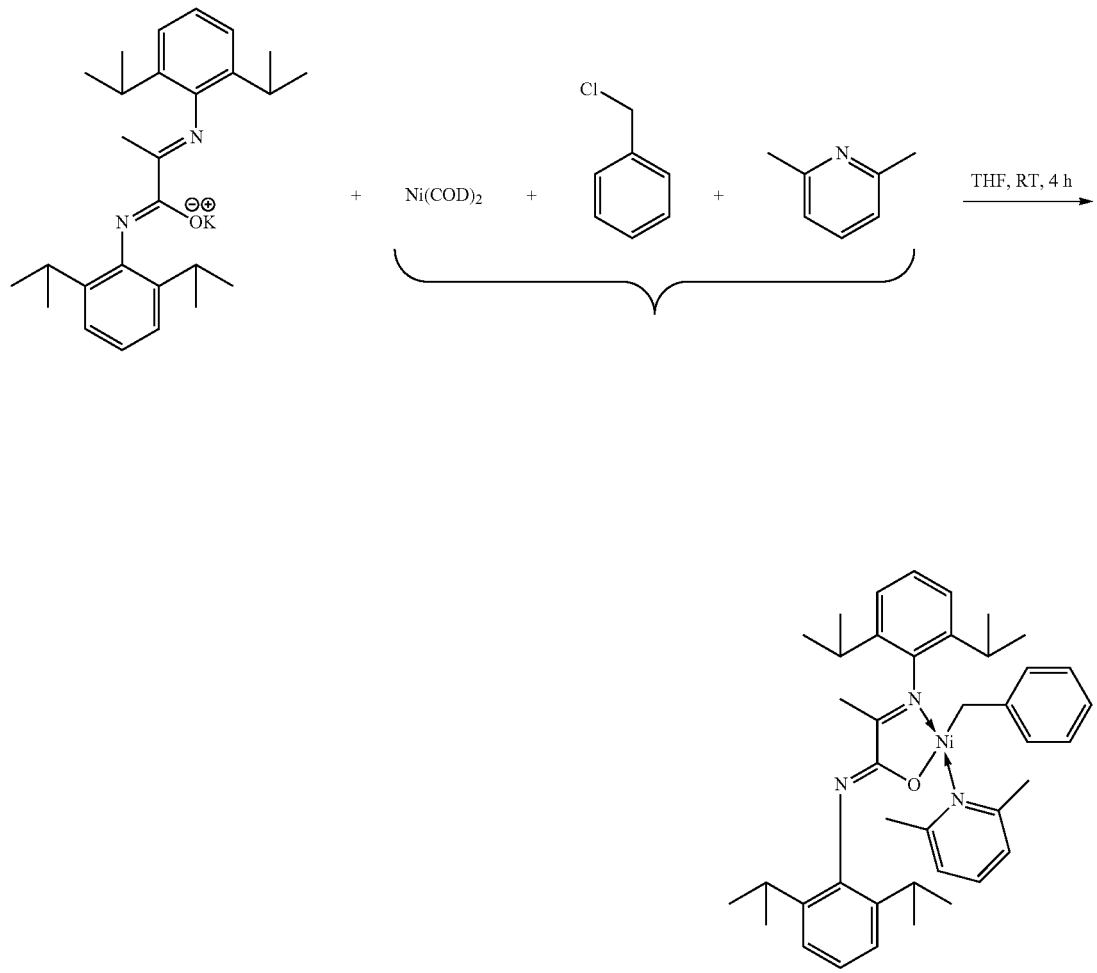

2

The synthesis of initiator 2 was carried out under an inert atmosphere with minimal exposure to light. A Ni(COD)₂ solution (68 mg, 0.25 mmol in 5 mL of THF) was treated with a mixture of benzyl chloride (63 mg, 0.63 mmol) and lutidine (156 mg, 1.45 mmol) in 2 mL of THF at 35° C. or ambient temperature. The potassium salt of the ligand (108 mg, 0.24 mmol, dissolved in 3 mL of THF) was added after 10 minutes. The reaction mixture was allowed to warm up to room temperature and was stirred overnight, volatiles were then removed under vacuum. The resulting oil was extracted with ether (15 mL) and filtered. The solvent volume was reduced and crystallization took place at room temperature overnight. Compound 2 was isolated from the first crystallization batch, as dark orange crystals in 71% yield.

¹H-NMR spectroscopy showed a single isomer. ¹H-NMR (399.95 MHz, [d₆]-benzene, 298 K): δ=7.11-7.04 (m, 5H), 6.90 (t, 1H), 6.75 (t, 1H), 6.58-6.50 (m, 4H), 6.23 (t, 1H), 5.84 (d, 2H), 3.89 (sep 2H), 3.66 (s, 6H), 3.49 (sep 2H), 2.09 (s, 3.0), 1.61 (d, 6H), 1.42 (s, 2H), 1.40 (d, 12H), 1.17(d, 6H). ¹³C-NMR (125.7 MHz, [d₆]-benzene, 298 K): δ=182.34, 158.79, 152.24, 141.93, 140.13, 138.64, 136.29, 127.86, 127.04, 124.52, 122.96, 122.88, 122.07, 29.73, 29.20, 26.67, 24.67, 24.34, 24.11, 21.09, 11.66.

Figure 2:
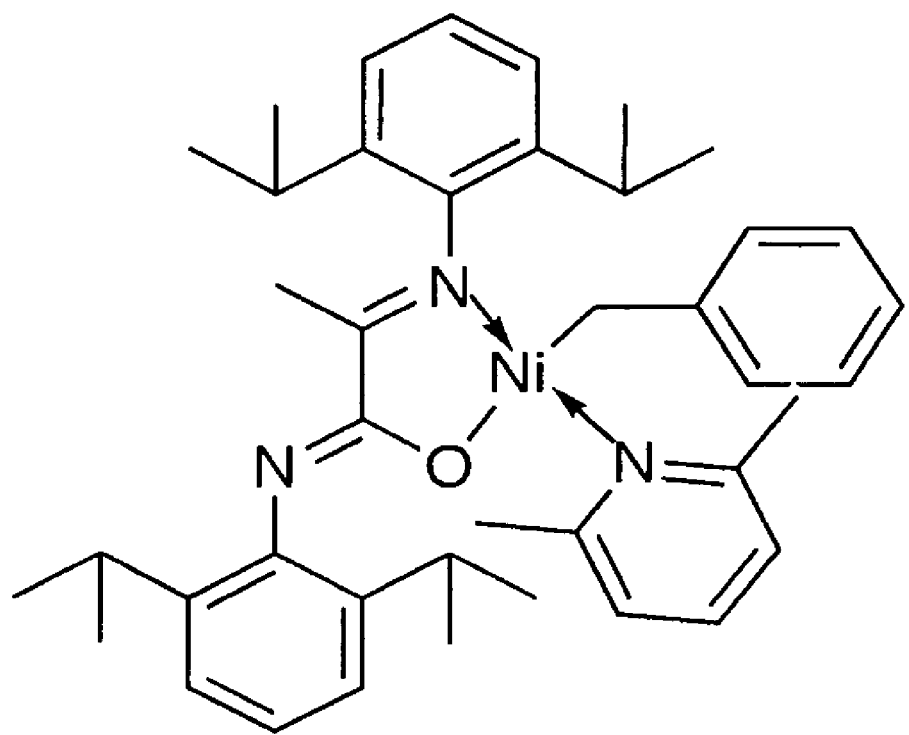
FIG. 2 shows a representation of the molecular structure of initiator 2 drawn at 50% probability. Hydrogen atoms not shown for clarity.

Solid-state characterization of initiator 2 by single crystal X-ray diffraction (FIG. 2) is consistent with an N,O-coordinated ligand. Initiator 2 adopts a square-planar coordination geometry around the nickel center with a cis relationship between the lutidine and the carboxamide nitrogen. The nitrogen atom in the lutidine fragment is displaced by 9° below of the N—Ni—O plane, while the benzyl ligand is 4° above the plane. The bond distances for Ni—C(28) and Ni—N(3) are approximately 0.023 Å longer, compared to those of initiator 1, similarly Ni—N(1) and Ni—O are 0.01 and 0.018 Å respectively.

Example 3

Catalytic initiator 3: [N-(2,6-Diisopropylphenyl)-2-(2,6-3,5-bisfluoromethylphenylimino) propanamidato-κ²N,O](η¹-CH₂Ph)nickel(2,6-dimethylpyridine)

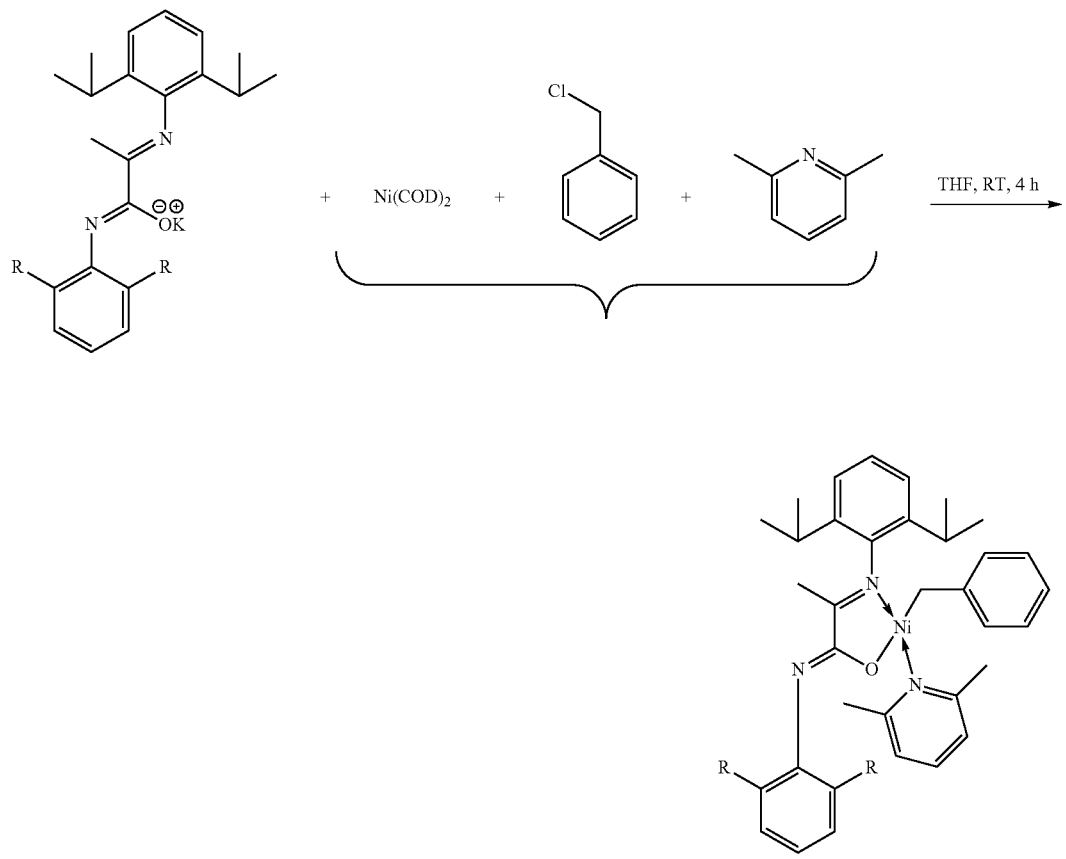

R = 3,5-CF₃C₆H₃

Figure 3:
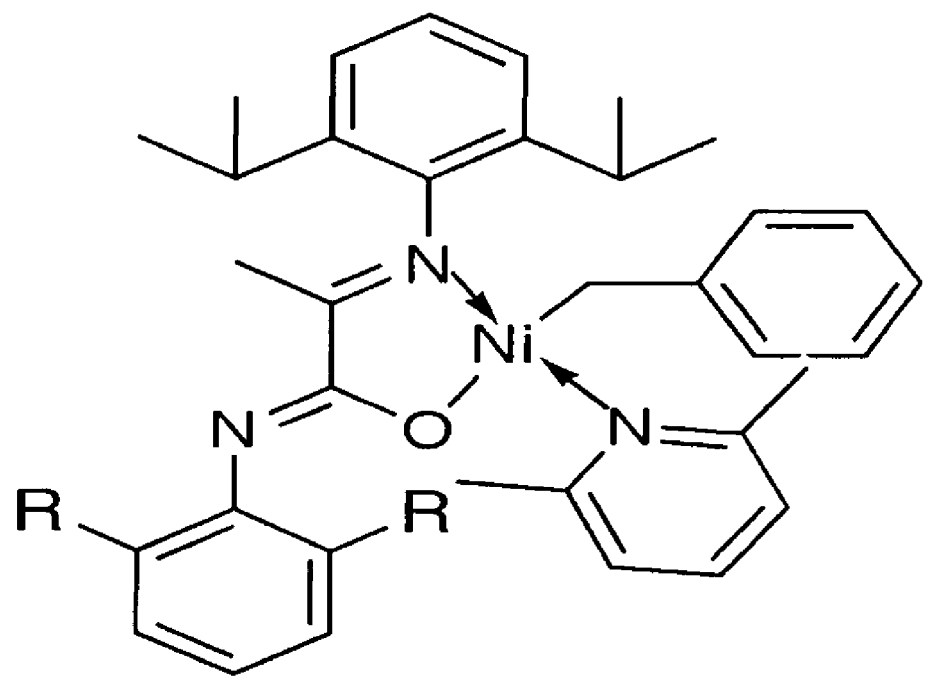
FIG. 3 shows a representation of the molecular structure of initiator 3 drawn at 50% probability. Hydrogen atoms not shown for clarity.

The synthesis of initiator 3 was carried out under an inert atmosphere with minimal exposure to light. A Ni(COD)₂ solution (68 mg, 0.25 mmol in 5 mL of THF) was treated with a mixture of benzyl chloride (63 mg, 0.5 mmol) and lutidine (160 mg, 1.48 mmol) in 2 mL of THF at ambient temperature. The potassium salt of the ligand (108 mg, 0.23 mmol, dissolved in 3 mL of THF) was added after 5 minutes. The reaction mixture was stirred overnight, volatiles were then removed under vacuum. The resulting oil was extracted with ether (15 mL) and filtered. The solvent was removed by vacuum. Pentane was added and crystallization took place at room temperature for 4 hours. initiator 3 was isolated from the first crystallization batch, as dark orange crystals in 50% yield. Single crystals of initiator 3 suitable for X-ray diffraction studies were obtained from ether by slow evaporation at room temperature and the results are shown in FIG. 3.

1H NMR spectroscopy showed a single isomer. ¹H-NMR (399.95 MHz, [d6]-benzene, 298 K): δ=8.06 (s, 2H), 8.04 (s, 4H), 6.98 (d, 2H), 6.90 (d, 1H), 6.88 (d, 1H), 6.80-6.77 (m, 3H), 6.75 (d, 2H), 6.63 (t, 2H), 6.29 (dd, 2H), 6.18 (t, 1H), 5.75 (d, 2H), 3.00 (3, 6H) 2.93 (sep 2H), 1.69 (s, 3.0), 1.19 (d, 12H), 1.08 (s, 2H). ¹³C-NMR (125.7 MHz, [d₆]-benzene, 298 K): δ=184.6, 162.09, 158.97, 150.82, 145.76, 142.51, 141.91, 138.28, 136.52, 133.22, 132.96, 132.64, 132.33, 130.37, 126.78, 125.58, 123.18, 122.78, 122.53, 121.69, 29.43, 25.97, 23.68, 21.93, 11.57.

Example 4

Catalytic initiator 4: [N-(2,6-Diisopropylphenyl)-2-(2,6-diisopropylphenylimino) propanamidato-κ²N, O] (η¹-benzoyl) nickel (pyridine)

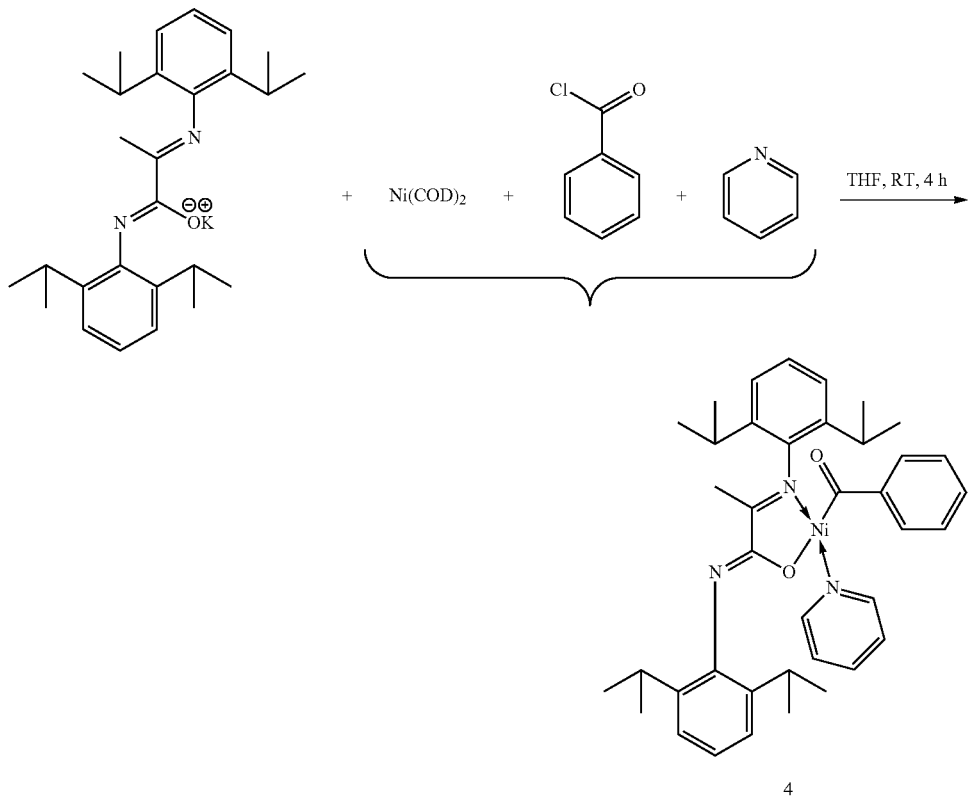

The synthesis of initiator 4 was carried out under an inert atmosphere with minimum exposure to light. A Ni(COD)₂ solution (112 mg, 0.41 mmol in 5 mL of THF) was treated with a mixture of benzoyl chloride (58 mg, 0.41 mmol) and pyridine (130 mg, 1.65 mmol) in 2 mL of THF at room temperature. After 15 minutes, the potassium salt of the ligand (140 mg, 0.31 mmol dissolved in 3 mL of THF) was added over 45 minutes. The reaction mixture was stirred overnight and volatiles were removed under vacuum. The resulting oil was extracted with ether (15 mL) and filtered. The solvent volume was reduced and crystallization took place at room temperature overnight. The product of the first crystallization batch contained initiator 4 with an impurity. Successive crystallizations from pentane-ether allowed for the isolation of initiator 4 as dark orange crystals in 54% yield.

$^1$H NMR spectroscopy showed one isomer. $^1$H-NMR (399.95 MHz, [d₆]-benzene, 298 K): δ=8.58 (d, 2H), 8.39-8.36 (tt, 2H) 7.29 (d, 2H), 7.02 (t, 1H), 6.96-6.89 (m, 6H), 6.24 (t, 1H), 5.85 (t, 2H), 3.86 (broad-sep 2H), 3.61 (sep 2H), 2.12 (s, 3.0), 1.46 (d, 12H), 1.25 (m, 6H), 1.11(d, 6H). $^{13}$C-NMR (125.7 MHz, [d₆]-benzene, 298 K): δ=250.98, 184.67, 162.60, 152.58, 151.35, 147.13, 143.45, 140.22, 139.18, 137.17, 131.29, 127.71, 125.67, 124.41, 124.19, 123.09, 29.90, 29.56, 25.21, 24.14, 23.59, 21.20.

Figure 4:
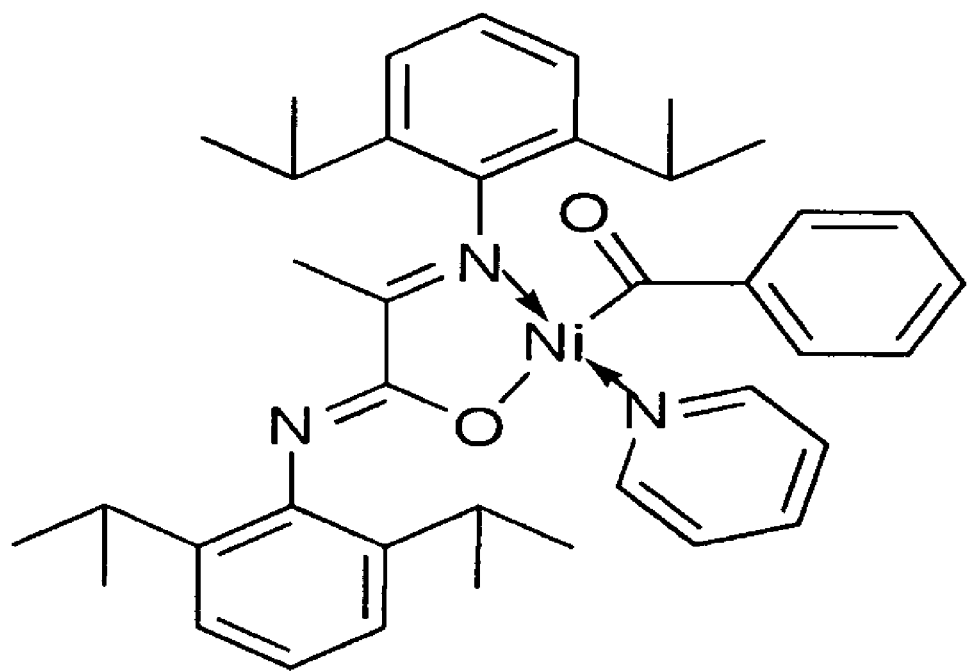
FIG. 4 shows a representation of the molecular structure of initiator 4 drawn at 50% probability. Hydrogen atoms not shown for clarity.

Single crystals of initiator 4 suitable for X-ray diffraction studies were obtained from ether by slow evaporation at room temperature and the results are shown in FIG. 4. The ligand is bound to the metal in an N, O coordination mode. The benzoyl group is coordinated in an η¹-fashion and is located trans to the amide, with the carbonyl perpendicular to the square planar arrangement surrounding the nickel center. The two aryl rings are also perpendicular to the square plane. The bond distances for Ni—N(2) and Ni—O(1) (1.912(3) Å and 1.934(2) Å, respectively) are similar to those in initiator 2. The Ni—N(3) bond distances for both complexes (nickel-lutidine, nickel-pyridine) are nearly identical (1.913 Å).

Example 7

Polymerization of Ethylene Using Catalytic Initiators 1-4

Polymerizations were conducted in the following manner using the initiators in examples 1-4. An autoclave reactor (100 mL) was loaded inside a glovebox with an appropriate amount (10 μmol) of a neutral nickel(II)-iminocarboxamide initiator (compounds shown in examples 1-4) with toluene, such that the final volume of the toluene solution was 30 mL. The reactor was sealed inside the glovebox. The reactor was attached to an ethylene line and the gas was fed continuously into the reactor at pressures ranging from 100 psi to 1000 psi. The pressurized reaction mixture was stirred at variable temperatures ranging from 20° C. to 100° C. After a specific reaction time, the ethylene was vented and acetone was added to quench the polymerization. The precipitated polymer was collected by filtration and dried overnight under vacuum. Table 1 below summarizes the polymerization reaction of ethylene with the aforementioned initiators in examples 1-4. (The molecular weight average and PDI's were determined by GPC analysis in dichlorobenzene at 135° C. and are relative to polystyrene standards).

TABLE 1

| Entry | Initiator | Reaction T. (° C.) | Activity (a) | Mw (b) | Mw/Mn |
|---|---|---|---|---|---|
| 1 | 1 | 40 | 60 | 62,900 | 1.8 |
| 2 | 2 | 20 | 43 | 124,600 | 1.8 |
| 3 | 2 | 40 | 304 | 143,460 | 2.2 |
| 4 | 3 | 40 | 280 | 160,500 | 1.9 |
| 5 | 4 | 40 | 270 | 145,360 | 1.7 |

(a)kg polymer/(mol Ni)(h), Polymerization reaction run at an ethylene pressure of 100 psi.
(b)The molecular weight of the polyethylene polymer was calculated by Refractive Index GPC Analysis (o-dichlorobenzene, 135° C.) relative to universal calibration from polystyrene standards.

Example 8

Copolymerization of Ethylene with Norbornene Derivatives

Method 1: Initial Addition of Comonomer

A steel reactor was loaded inside a glovebox with an appropriate amount (10 μmol) of a neutral nickel(II)-iminocarboxamide initiator (compounds shown in examples 1-4), 5-norbornen-2-yl acetate (A) or 5-norbornen-2-ol (B) (0.075 M to 0.5 M), and toluene (26 g) such that the total volume of the toluene solution was 30 mL. The steel reactor was sealed inside the glovebox and was attached to the ethylene line. Ethylene was fed continuously into the reactor at 100 psi to 400 psi and the pressurized reaction mixture was stirred at temperatures ranging from 20° C. to 80° C. Ethylene was vented after 20 min, and acetone and methanol were added to quench the polymerization. The precipitated polymer was collected by filtration and dried under high vacuum for 12 h. Table 2 below summarizes the copolymerizations reaction using initiator 2.

TABLE 2

| Entry | Initiator | Comonomer Concentration (mol/L) | Reaction T. (° C.) | Activity (a) | Mw (b) | Mw/Mn | Incorp. (mol %) (c) |
|---|---|---|---|---|---|---|---|
| 1 | 2 | A (0.075) | 40 | 160 | 96,450 | 1.9 | 8.6 |
| 2 | 2 | A (0.150) | 40 | 170 | 93,160 | 1.8 | 13.0 |
| 3 | 2 | B (0.075) | 40 | 147 | 88,184 | 2.0 | 7.8 |
| 4 | 2 | B (0.150) | 40 | 48 | 183,400 | 5.7 | 13.6 |

(a)kg polymer/(mol Ni)(h), Polymerization reaction run at an ethylene pressure of 100 psi.
(b)The molecular weight of the polyethylene polymer was calculated by Refractive Index GPC Analysis (o-dichlorobenzene, 135° C.) relative to universal calibration from polystyrene standards.
(c)Mol % incorporation of norbornenyl group, calculated from $^1$H-NMR spectroscopy ($C_6D_6$/o-dichlorobenzene, 120° C.):

Method 2: Addition of Comonomer After Initiation with Ethylene

Initiator solutions were prepared as described above, however the comonomer was added via an addition funnel after the polymerization of ethylene was allowed to run for a specific time. Table 3 summarizes copolymerization reaction of ethylene with 5-norbornen-2-yl acetate (A) or 5-norbornen-2-ol (B) using the initiators in examples 1-4. Polymerization was quenched as described in method 1.

TABLE 3

| Entry | Initiator | Comonomer Concentration (mol/L) | Reaction T. (° C.) | Activity (a) | Mw (b) | Mw/Mn | Incorp. (mol %) (c) |
|---|---|---|---|---|---|---|---|
| 1 | 4 | A (0.075) | 40 | 261 | 125,077 | 2.5 | 2.5 |
| 2 | 4 | B (0.075) | 40 | 323 | 111,800 | 2.6 | 2.8 |

(a)kg polymer/(mol Ni)(h), Polymerization reaction run at an ethylene pressure of 400 psi.
(b)The molecular weight of the polyethylene polymer was verified by Refractive Index GPC Analysis (o-dichlorobenzene, 135° C.) relative to universal calibration from polystyrene standards.
(c)Mol % incorporation of norbornenyl group, calculated from $^1$H-NMR spectroscopy ($C_6D_6$/o-dichlorobenzene, 120° C.):

REFERENCES

The following publications are hereby incorporated by reference:

1. Ittel, S. D., Johnson, L. K., Brookhart, M. Chem. Rev. 2000, 100, 1169 (and references therein);
2. Gates, D. P., Svejda, S., Onate, E., Killian, C. M., Johnson, L. K., White, P. S., Brookhart, M. Macromolecules, 2000, 33, 2320;
3. Svejda, S. A., Johnson, L. K., Brookhart, M. J. Am. Chem. Soc. 1999, 121, 10634;
4. Younkin, F.; Connor, E. F.; Henderson, J. I.; Friedrich, S. K.; Grubbs, R. H.; Bansleben, D. A. Science, 2000, 287, 460; WO 9842664; WO 9842665;
5. Rieger, B.; Baugh, L.; Striegler, S.; Kacker, S. Late Transition Metal Polymerization Catalysis; John Wiley & Sons: New York, 2003.
6. Blom, R.; Follestad, A.; Rytter, E.; Tilset, M.; Ystenes, M. Organometallic Catalysts and Olefin Polymerization: Catalysts for a New Millennium; Springer-Verlag: Berlin, Germany, 2001.
7. Galli, P.; Vecellio, G. J. Polym. Sci. Part A: Polym. Chem. 2004, 42, 396.
8. Keim, W.; Kowalt, F. H.; Goddard, R.; Kruger, C. Angew. Chem., Int. Ed. Engl. 1978, 17, 466.
9. Bonnet, M. C.; Dahan, F.; Ecke, A.; Keim, W.; Schultz, R. P.; Tkatchenko, I. Chem Commun. 1994, 615.
10. Boffa, L. S.; Novak, B. M. Chem. Rev. 2000, 100, 1479.
11. Yanjarappa, M. J.; Sivaram, S. Prog. Polym. Sci. 2002, 27, 1347.
12. Mecking, S.; Held, A.; Bauers, F. M. Angew. Chem., Int. Ed. 2002, 41, 544.
13. Gibson, V. C.; Spitzmesser, S. K. Chem. Rev. 2003, 103, 283. 283
14. Mecking, S. Coordination Chemistry Reviews 2003, 203, 325.
15. SMART Software Users Guide, Version 5.1, Bruker Analytical X-Ray Systems, Inc.; Madison, Wis. 1999.
16. SAINT Software Users Guide, Version 6.0, Bruker Analytical X-Ray Systems, Inc.; Madison, Wis. 1999.
17. Sheldrick, G. M. SADABS, Version 2.05, Bruker Analytical X-Ray Systems, Inc.; Madison, Wis. 2001.
18. Sheldrick, G. M. SHELXTL Version 6.12, Bruker Analytical X-Ray Systems, Inc.; Madison, Wis. 2001.
19. International Tables for X-Ray Crystallography 1992, Vol. C., Dordrecht: Kluwer Academic Publishers.
20. Flack, H. D. Acta. Cryst. 1983 A39, 876.

21. (a) S. J. Diamanti, P. Ghosh, F. Shimizu, and G. C. Bazan, Macromolecules, 2003, 36, 9731-9735. (b) S. J. Diamanti, V. Khanna, A. Hotta, D. Yamakawa, F. Shimizu, E. J. Kramer, G. H. Fredrickson, and G. C. Bazan. J. Am. Chem. Soc., 2004, 126, 10528-10529.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

The invention claimed is:

1. A catalyst for the polymerization and co-polymerization of an olefin, comprising the general formula

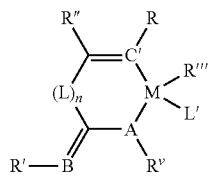

where:
M is a late transition metal ion selected from the group consisting of Fe, Co, Ni, Pd and Cu,
A is oxygen, nitrogen, phosphorus, or sulfur,
B is nitrogen or phosphorus,
C' is nitrogen, phosphorus, or carbon,
L is a saturated or unsaturated bridging hydrocarbon or aromatic unit,
R and R' are each independently a $C_1$-$C_{24}$ hydrocarbon selected from the group consisting of alkyl, alkene, hydrocarbyl, cycloalkyl, aryl and substituted aryl; wherein the aryl substituents may be functionalized groups that increase or decrease the electron density or modify the steric encumbrance at C',
R" is a hydrocarbon,
L' represents a neutral monodentate $2e^-$ N-base donor ligand, or a neutral monodentate $2e^-$ O-base ligand,
R''' is a hydrocarbon,
R''' and L' may be combined into a single chelating fragment,
$R^v$=R only when A=phosphorous or nitrogen, and is nothing when A=oxygen or sulfur,
n=0-3, and
whereby said catalyst is phosphine-free and non-ionic.

2. The catalyst of claim 1, wherein the late transition metal is Ni.

3. The catalyst of claim 1, wherein the catalyst is selected from the group consisting of N-(2,6-Diisopropylphenyl)-2-(2,6-diisopropylphenylimino)propanamidato-$\kappa^2$N,O($\eta^1$-CH$_2$Ph)nickel(pyridine), [N-(2,6-Diisopropylphenyl)-2-(2,6-diisopropylphenylimino)propanamidato-$\kappa^2$N,O] ($\eta^1$CH$_2$Ph)nickel(2,6-dimethylpyridine), [N-(2,6-Diisopropylphenyl)-2-(2,6-3,5-bisfluoromethylphenylimino)propanamidato-$\kappa^2$N,O]($\eta^1$-CH$_2$Ph)nickel(2,6-dimethylpyridine), and [N-(2,6-Diisopropylphenyl)-2-(2,6-diisopropylphenylimino) propanamidato-$\kappa^2$N,O]($\eta^1$-benzoyl)nickel(pyridine).

4. The catalyst of claim 1, wherein R" is a $C_1$-$C_{24}$ hydrocarbon selected from the group consisting of alkyl, alkene, hydrocarbyl, cycloalkyl, aryl, substituted aryl, O-hydrocarbon, O-aryl, and O-substituted aryl.

5. The catalyst of claim 1, wherein claim 1, is selected from the group consisting of

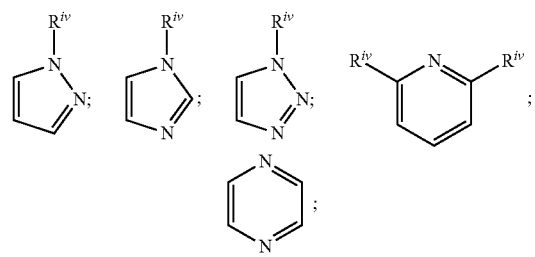

O=P($R^{iv}$)$_3$; $R^{iv}$CO$R^{iv}$, furan; $R^{iv}$O$R^{iv}$, 1,4-dioxane, and ($R^{iv}$)$_3$NO, wherein $R^{iv}$ is a hydrogen, hydrocarbon, alkyl, alkene, hydrocarbyl, cycloalkyl, aryl or substituted aryl.

6. The catalyst of claim 1, wherein R''' is selected from the group consisting of alkyl, alkene, hydrocarbyl, allyl, aryl, substituted aryl, benzyl, substituted benzyl, (C=O)-alkyl, (C=O)-aryl and substituted (C=O)-aryl.

7. The catalyst of claim 4, wherein the substituted aryl and O-substituted an contain halogen as a substituent.

* * * * *

UNITED STATES PATENT AND TRADEMARK OFFICE
CERTIFICATE OF CORRECTION

| | | |
|---|---|---|
| PATENT NO. | : 7,968,487 B2 | Page 1 of 1 |
| APPLICATION NO. | : 11/649949 | |
| DATED | : June 28, 2011 | |
| INVENTOR(S) | : Bazan et al. | |

It is certified that error appears in the above-identified patent and that said Letters Patent is hereby corrected as shown below:

In the Specification

Column 2

Line 16, please delete "R" represents a hydrocarbon $C_1$-$C_{24}$ hydrocarbon" and insert --R" represents a $C_1$-$C_{24}$ hydrocarbon--;

Column 3

Line 50, please delete "R" represents a hydrocarbon $C_1$-$C_{24}$ hydrocarbon" and insert --R" represents a $C_1$-$C_{24}$ hydrocarbon--; and In the Claims Column 16

Line 44, please delete "O-substituted an" and insert --O-substituted aryl--.

Signed and Sealed this
Twentieth Day of May, 2014

Michelle K. Lee
*Deputy Director of the United States Patent and Trademark Office*